United States Patent
Köhler et al.

(10) Patent No.: US 11,719,776 B2
(45) Date of Patent: Aug. 8, 2023

(54) PROVISION OF POSITION INFORMATION OF A LOCAL RF COIL

(71) Applicant: Siemens Healthcare GmbH, Erlangen (DE)

(72) Inventors: Michael Köhler, Nuremberg (DE); Johann Sukkau, Herzogenaurach (DE); Michael Wullenweber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 22 days.

(21) Appl. No.: 17/490,206

(22) Filed: Sep. 30, 2021

(65) Prior Publication Data

US 2022/0099766 A1    Mar. 31, 2022

(30) Foreign Application Priority Data

Sep. 30, 2020  (DE) .......................... 102020212316.0
Nov. 4, 2020   (DE) .......................... 102020213900.8

(51) Int. Cl.
  *G01R 33/34*   (2006.01)
  *A61B 5/055*   (2006.01)
  *G01R 33/56*   (2006.01)

(52) U.S. Cl.
  CPC ........ *G01R 33/34092* (2013.01); *A61B 5/055* (2013.01); *G01R 33/5608* (2013.01)

(58) Field of Classification Search
  CPC .............. A61B 5/055; G01R 33/34092; G01R 33/5608
  See application file for complete search history.

(56) References Cited

U.S. PATENT DOCUMENTS

| | | |
|---|---|---|
| 5,936,406 A | 8/1999 | Potthast |
| 2003/0184292 A1 | 10/2003 | Meyer et al. |
| 2005/0253584 A1 | 11/2005 | Campagna |
| 2007/0103157 A1 | 5/2007 | Campagna |
| 2008/0211502 A1 | 9/2008 | Arnold et al. |
| 2015/0196222 A1* | 7/2015 | Stehning ............ A61N 5/1039 600/411 |
| 2017/0315197 A1 | 11/2017 | Schneider |
| 2018/0144467 A1* | 5/2018 | Sofka ................. G06K 9/6269 |
| 2021/0382157 A1* | 12/2021 | Luijten ................ G10K 11/34 |

FOREIGN PATENT DOCUMENTS

| | | |
|---|---|---|
| DE | 19653535 C1 | 6/1998 |
| DE | 102004022559 B4 | 5/2006 |
| DE | 102005052564 A1 | 5/2007 |
| DE | 10207736 B4 | 7/2007 |
| DE | 102007010274 B4 | 11/2010 |
| DE | 102016207351 A1 | 11/2017 |
| DE | 102019110733 A1 | 10/2020 |

OTHER PUBLICATIONS

German Patent Office, Office Action issued for DE 102020213900.8, 6 pgs., dated: Jul. 15, 2021.

* cited by examiner

*Primary Examiner* — Gregory H Curran
(74) *Attorney, Agent, or Firm* — Banner & Witcoff Ltd.

(57) ABSTRACT

A computer-implemented method for provision of a result dataset having position information of a local radio-frequency coil, including: providing input data having at least magnetic resonance data, which is acquired by means of the local radio-frequency coil; determining a result dataset by applying a trained function to the input data, wherein the result dataset comprises position information for determining the position of the local radio-frequency coil; and providing the result dataset.

20 Claims, 4 Drawing Sheets

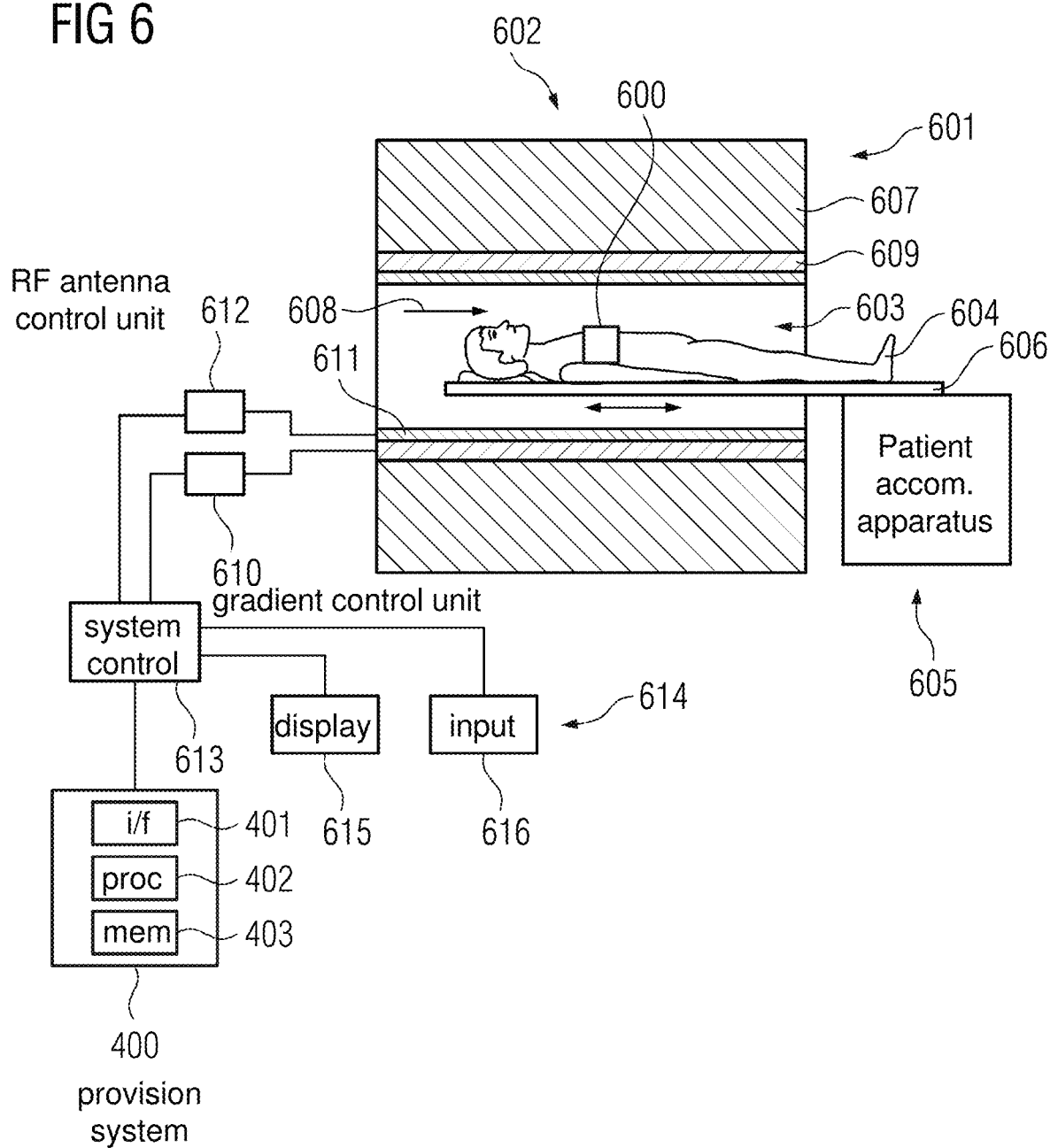

PROVISION OF POSITION INFORMATION OF A LOCAL RF COIL

TECHNICAL FIELD

The present disclosure relates to a computer-implemented method for provision of a result dataset comprising position information of a local radio-frequency coil. Furthermore the present disclosure relates to a computer-implemented method for provision of a trained function, which is embodied to determine position information of a local radio-frequency coil. The disclosure is further based on a provision system for provision of the position information and also on a magnetic resonance apparatus with the provision system. The disclosure furthermore comprises a corresponding computer program product and a corresponding computer-readable memory medium.

BACKGROUND

For magnetic resonance examinations of a patient it is frequently helpful for a position to be known of a local radio-frequency coil that is arranged for the magnetic resonance examination around the region of the patient to be examined. This is especially true when different local radio-frequency coils are positioned on the patient for different magnetic resonance measurements. Only a part of the local radio-frequency coils or also only individual coil elements of a local radio-frequency coil are used here for each magnetic resonance measurement. If for example magnetic resonance image data of different organs is acquired during a magnetic resonance examination, then it is of advantage in each case only to activate those local radio-frequency coils and/or coil elements of a local radio-frequency coil that are located especially close to the respective organ to be examined.

It therefore makes sense to automatically detect the position of the local radio-frequency coils and/or of individual coil elements of the local radio-frequency coils. The position of the individual local radio-frequency coils and/or of individual coil elements of the local radio-frequency coils can be shown to a user for example together with a rough initial magnetic resonance image of the patient. On the basis of the position of the individual local radio-frequency coils and/or of individual coil elements of the local radio-frequency coils, the user can select those of the local radio-frequency coils and/or of individual coil elements of the local radio-frequency coils that lie closest to the desired examination region. Moreover the local radio-frequency coils and/or the individual coil elements of the local radio-frequency coils can be selected automatically, as is known for example from patent DE 10 2007 010 274 B4.

The position of the local radio-frequency coil is computed and/or determined in this case from the distribution of the measured signal as a function of the location. The receive sensitivity of a local radio-frequency coil can vary sharply and in general decreases as the distance from the local radio-frequency coil increases. Therefore the signal measured by a local radio-frequency coil falls as a rule as the distance from it increases. The maximum of the signal as a function of the location then generally corresponds to the position of the local radio-frequency coil.

Problems can occur however in the determination of the position of the local radio-frequency coils and/or of individual coil elements of the local radio-frequency coils, which lead to inaccuracies and/or a falsification of the position of the local radio-frequency coils and/or of individual coil elements of the local radio-frequency coils. For example it can be that a relationship between a maximum of a measured signal and the position of the local radio-frequency coil is not always clearly available. Different volumes and/or tissue types can bring about and/or influence a location dependency of the created signal here. For example less of a signal is created from the extremities of a patient because of the smaller number of spins than from the region of the abdomen. This means that it can occur that the maximum signal is not measured directly at the position of the local radio-frequency coil, but somewhat offset from it.

A further reason for positional inaccuracies can be that, with increasing distance from the isocenter, a basic magnetic field and a spatial encoding of a gradient coil deviate from a target value. In such cases inhomogeneities of the magnetic field and non-linearities of the gradient coil lead to the spatial encoding and thus the measured position being able to be falsified as the distance from the center of a scanner unit of a magnetic resonance apparatus increases.

A further reason for positional inaccuracies can be that a local radio-frequency coil at a great distance from a center of the magnetic resonance apparatus also receives and/or delivers only a small signal and thus the measured spectrum can be dominated by noise signals. This can likewise lead to an incorrect localization.

SUMMARY

An underlying object of the present disclosure is to specify improved options for determining the position of local radio-frequency coils and/or of individual coil elements of a local radio-frequency coil for a magnetic resonance measurement. The object is achieved by the features of the independent claims. Advantageous aspects are described in the dependent claims.

The disclosure is based on a computer-implemented method for provision of a result dataset comprising position information of a local radio-frequency coil, comprising the following steps:
- provision of input data, wherein the input data comprises at least magnetic resonance data, which is acquired by means of the local radio-frequency coil,
- determination of a result dataset by application of a trained function to the input data, wherein the result dataset comprises position information for determining a position of the local radio-frequency coils, and
- provision of the result dataset.

The provision of the input data comprising at least magnetic resonance data acquired by means of the local radio-frequency antenna and a receipt of the trained function is done in particular by means of an interface, in particular by means of an interface of a provision system. The determination of the result dataset is preferably done by means of a determination unit and/or a processing unit, in particular by means of a determination unit and/or a processing unit of the provision system.

The input data preferably comprises magnetic resonance data, which is acquired by means of the local radio-frequency coil and/or individual coil elements of the local radio-frequency coil. In this case the input data can also comprise magnetic resonance data, which is acquired by means of two or more local radio-frequency coils and/or also by means of two or more coil elements of a local radio-frequency coil. The input data can moreover also comprise additional information, such as for example which local radio-frequency coil and/or which coil elements of the local radio-frequency coil have been used for the acquisition of the magnetic resonance data included in the input data. The input data can moreover also comprise additional information, such as, for example, a region of the patient to be examined and/or a couch position and/or further, information appearing sensible to the person skilled in the art. The term local radio-frequency coil is to be understood as both a local radio-frequency coil and also as individual coil elements of a local radio-frequency coil.

Other terms for trained function are trained mapping specification, mapping specification with trained parameters, function with trained parameters, algorithm based on artificial intelligence, machine-learning algorithm. An example of a trained function is an artificial neural network, wherein weights and/or edge weights of the artificial neural network correspond to the parameters of the trained function. Instead of the term "neural network" the term "neural net" can also be used. In particular a trained function can also be a deep neural network or deep artificial neural network. A further example of a trained function is a Support Vector Machine, other machine learning algorithms are furthermore also in particular able to be used as a trained function.

In this way the provision of a result dataset comprising position information of a local radio-frequency coil is based in particular on a machine learning method, also called a deep-learning method, which is based on the artificial neural network. An artificial neural network (ANN) is in particular a network of artificial neurons emulated in a computer program. The artificial neural network is typically based in this case on a networking of a number of artificial neurons. The artificial neurons in this case are typically arranged on different layers. Usually the artificial neural network comprises an input layer and an output layer, of which the neuron output is visible as the only output of the artificial neural network. Layers lying between the input layer and the output layer are typically referred to as hidden layers. Typically an architecture and/or topology of an artificial neural network is first initiated and is then trained in a training phase for a specific task or for a number of tasks in a training phase. The training of the artificial neural network in this case typically comprises changing a weighting and/or a parameterization of a connection between two artificial neurons of the artificial neural network. The training of the artificial neural network can also comprise a development of new connections between artificial neurons, a removal of existing connections between artificial neurons, an adaptation of threshold values of the artificial neurons and/or an insertion and/or deletion of artificial neurons.

The trained function and/or the artificial neural network in this case can also comprise a fully connected neural net, in which each neuron of a layer is linked to each neuron of the preceding layer and of the succeeding layer.

Furthermore the trained function and/or the artificial neural network can also comprise hidden layers, which are embodied as drop-out layers. Such drop-out layers comprise a regularization method in order to reduce and/or to prevent an overfitting of the trained function and/or of the artificial neural network. Here, during the training of the trained function and/or of the artificial neural network, individual neurons in the drop-out layers chosen at random are deactivated and not taken into account for the coming computation step.

The trained function and/or the artificial neural network can furthermore comprise hidden layers, which comprise recurrent LSTM (long short-term memory) neurons. Here there can be a feedback between the neurons of different layers. This variant of the trained function and/or the artificial neural network above all comprises an effective learning phase, by the in particular multilayer pure feed-forward networks, i.e. in multilayer networks without feedback, the problem of parameters and/or weights of the front hidden layers only being able to be unsatisfactorily optimized, reduced and/or prevented during the learning phase.

The trained function and/or the artificial neural network has in particular already been trained suitably in advance for the determination of position information for determining the position of the local radio-frequency coil on the basis of the acquired magnetic resonance data. For the training of the trained function and/or of the artificial neural network in this case training datasets are used in particular, to which for example a signal intensity of magnetic resonance data of a position acquired by means of the local radio-frequency coil and/or position information of the local radio-frequency coil is assigned. The training datasets in this case are typically acquired from persons and/or training radio-frequency coils which differ from the patient.

The trained function and/or the artificial neural network maps the input data to output data, in particular to the result dataset. Here the output data, in particular the result dataset, can in particular furthermore depend on a parameter or a number of parameters of the trained function. The parameter or the number of parameters of the trained function and/or of the artificial neural network can be determined and/or adapted by training. The determination and/or the adaptation of the one parameter or of the number of parameters of the trained function can be based in particular on a pair consisting of training input data and associated training output data, wherein the trained function is applied to the training input data for creation of training output data. In general a trainable function, i.e. a function with one or more parameters not yet adapted, is referred to as a trained function.

The trained function and/or the artificial neural network comprises at least one parameter, wherein the output values of the trained function and/or of the artificial neural network are dependent on the value or the values of the at least one parameter. A parameter of the trained function and/or of the artificial neural network is based in particular on the at least one training dataset if the parameter of the trained function and/or of the artificial neural network has been changed and/or adapted for optimizing the trained function and/or the artificial neural network based on the at least one training dataset. This includes the case in which a number or all parameters of the trained function and/or of the artificial neural network have been changed and/or adapted for optimization based on the at least one training dataset.

The result dataset comprises the position information for determining the position of the local radio-frequency coil. The result dataset in this case can also directly comprise the position of the local radio-frequency coil. Moreover, the result dataset can also comprise further information regarding the position of the local radio-frequency coil. For example the result dataset here can also comprise information that specifies how likely there is to be a match between the position of the local radio-frequency coil established from the position information and the actual position of the local radio-frequency coil. Moreover it can also be that the result dataset also contains information that no local radio-frequency coil and/or no coil element of a local radio-frequency coil could be determined on the basis of the input data or that a position could not be determined for any local radio-frequency coil and/or any coil element of a local radio-frequency coil on the basis of the input data. In such a case the position information can assume the value "0".

The disclosure advantageously enables a position recognition and/or a position determination of a local radio-frequency coil and/or of coil elements of a local radio-frequency coil and also an identification of local radio-frequency coils and/or of coil elements of a local radio-frequency coil to be carried out reliably. In particular with local radio-frequency coils that are arranged and/or positioned outside a homogeneity volume and/or outside a linearity volume during magnetic resonance data acquisition, the position recognition and/or the position determination as well as the identification of local radio-frequency coils and/or of coil elements of a local radio-frequency coil can be carried out especially efficiently. A further advantage is that the position recognition and/or the position determination and also the identification of local radio-frequency coils and/or of coil elements of a local radio-frequency coil is independent of a sensor system for recognition and/or detection of the local radio-frequency coils, such as for example cameras or sensors attached to the local radio-frequency coils. Moreover the disclosed method can also be applied especially easily to local radio-frequency coils of other manufacturers, so that these local radio-frequency coils do not have to be equipped with a corresponding sensor system.

Compared to additional measurements for determining the position of the local radio-frequency coil from the prior art, the disclosed method for provision of a result dataset comprising position information of a local radio-frequency coil has the advantage that a lower maintenance effort is required. This is because these additional and/or dedicated measurements require threshold values in particular to be set and/or defined. These threshold values contribute to the decision about whether a local radio-frequency coil is available for a medical magnetic resonance measurement or whether the local radio-frequency coil is too far away for the medical magnetic resonance measurement from the center of the scanner unit. However, such threshold values are in particular dependent on a type of local radio-frequency coil and on a region of the body to be examined. It has been shown that such threshold values are not always reliable, and that, depending on the patient type and/or further factors, the result can be inaccuracies and/or deviations in the determination of the threshold values and/or the position of the local radio-frequency coil. Through the use of the method proposed here for provision of a result dataset comprising position information of a local radio-frequency coil by means of a trained function and/or an artificial neural network, the setting and/or the definition of suitable threshold values is replaced by automatic training.

In an advantageous development of the disclosed method for provision of a result dataset comprising position information of a local radio-frequency coil there can be provision for the input data provided to comprise magnetic resonance data acquired by means of the local radio-frequency coil, wherein the magnetic resonance data comprises position information in at least one spatial direction. The position information of the magnetic resonance data preferably comprises a spatial encoding of the magnetic resonance data acquired. For example, the magnetic resonance data with position information, in particular spatial encoding, is acquired by means of a spin echo measurement and/or a gradient echo measurement. The position information, in particular the spatial encoding, of the magnetic resonance data can be undertaken in this case in one spatial direction or in a number of spatial directions. The magnetic resonance data with position information, in particular a spatial encoding, in number of spatial directions and/or a number of position coordinates can be present for each spatial direction and/or each position coordinate as separate magnetic resonance data, in particular a separate spectrum. As an alternative or in addition it is also conceivable for the magnetic resonance data with position information, in particular a spatial encoding, to be present in a number of spatial directions and/or a number of position coordinates as multidimensional magnetic resonance data, in particular as a multidimensional spectrum. The magnetic resonance data, in particular the spectra, can further be present already Fourier-transformed or also in k-space encoding. Preferably here the number of input neurons of the input layer of the trained function and/or of the artificial neural network corresponds to the number of data points of the input data, in particular the magnetic resonance data and/or the spectra. This aspect of the disclosure enables a high positional accuracy to be achieved in the determination of the position information of the local radio-frequency coils and/or of coil elements of the local radio-frequency coil and thus a high level of efficiency of the disclosed method for provision of a result dataset comprising position information of a local radio-frequency coil can be provided. In particular here the position information of the local radio-frequency coil, in particular the position of the local radio-frequency coil, can be determined sequentially for each spatial direction or also jointly for all spatial directions.

In an advantageous development of the disclosed method for provision of a result dataset comprising position information of a local radio-frequency coil there can be provision for the input data provided to comprise magnetic resonance data acquired by means of the local radio-frequency coil, wherein the magnetic resonance data is normalized with regard to magnetic resonance data of a homogeneous radio-frequency coil. The homogeneous radio-frequency coil comprises a body coil, for example. In particular here a receive profile of acquired magnetic resonance data and/or acquired signals of the body coil is more homogeneous than for example a receive profile of acquired magnetic resonance data and/or acquired signals of a knee coil and/or of further local radio-frequency coils. A normalization of the acquired magnetic resonance data can for example comprise a division of the magnetic resonance data acquired by means of the local radio-frequency coil, in particular magnetic resonance data with a spatial encoding, by the magnetic resonance data and/or signals acquired with the homogeneous radio-frequency coil, in particular the body coil, for each position point. The magnetic resonance data and/or signals of the homogeneous radio-frequency coil can also be acquired in this case separately from the acquisition of the magnetic resonance data by means of the local radio-frequency coil.

This aspect of the disclosure advantageously enables a positional accuracy of the acquired magnetic resonance data, because of for example spatial variations of tissue types and/or spatial variations of the extent of the region to be examined, to be minimized. This also enables a reliable determination of position information and/or determination of the position of the local radio-frequency coil and/or of coil elements of the local radio-frequency coil to be made possible for the regions to be examined, such as for example the extremities of the patient.

In an advantageous development of the disclosed method for provision of a result dataset comprising position information of a local radio-frequency coil there can be provision for the input data provided to comprise magnetic resonance data acquired by means of the local radio-frequency coil, wherein the magnetic resonance data comprises non-position-encoded magnetic resonance data with different measurement frequencies. The magnetic resonance data in this case can comprise a measurement frequency, which comprises an average resonant frequency in the volume close to the center of a scanner unit of a magnetic resonance apparatus. Moreover the magnetic resonance data can also comprise measurement frequencies that deviate from the average resonant frequency. Through this in particular local radio-frequency coils and/or coil elements of a local radio-frequency coil, which are preferably arranged and/or positioned outside a homogeneity region and/or linearity region of the scanner unit of the magnetic resonance apparatus, can be reliably identified. If the magnetic resonance data in such a measurement exhibits a significant signal, this can serve as an indication that the local radio-frequency coil concerned and/or the coil elements of a local radio-frequency coil concerned are located too far away from the center, in particular the isocenter and/or the FOV, of the scanner unit and should not be used any further for a reliable position determination.

Moreover it can also be that the input data is already pre-processed, such as for example by smoothing and/or filtering of the input data, in particular of the magnetic resonance data acquired by means of the local radio-frequency coil.

In an advantageous development of the disclosed method for provision of a result dataset comprising position information of a local radio-frequency coil there can be provision for the input data provided to comprise at least one further item of coil information. The at least one further item of coil information can for example comprise a coil type of the local radio-frequency coil used and/or current couch position and/or an examination region on the patient and/or data that is made available by a user for the current examination. As an alternative or in addition the input data provided and/or the further coil information can also comprise a position of the patient and/or anatomy information of the patient. The anatomy information preferably comprises a size and/or an extent of the patient. In particular this enables a reliable recognition and/or determination of the position information to be achieved. For example the further coil information of a region of the body that is likely to have been examined can lead to a different weighting of the acquired signal spectra and/or of the signal-to-noise ratio in the determination of the position information, since the acquired signal spectra and/or the signal-to-noise ratio exhibit marked differences depending on the region of the body examined. For example the spectra and/or the signal-to-noise ratios differ markedly for an examination of the hand compared to the spectra and/or the signal-to-noise ratios for an examination of the abdomen. Moreover, with the use of different coil combinations, different parameterizations and/or weightings of the trained function and/or of the artificial neural network can be used. If for example the local radio-frequency coils of type A and type B are used together for a measurement, this data can be passed together to the trained function and/or to the artificial neural network. Thus a different parameterization and/or weighting is used than when local radio-frequency coils of type A and C or just one local radio-frequency coil of type A is used on its own. Parameterization and/or weighting stands here for a set of parameters and/or weights between the individual neurons of the trained function and/or of the artificial neural network as well as for the activity functions of the neurons.

In an advantageous development of the disclosed method for provision of a result dataset comprising position information of a local radio-frequency coil there can be provision for the result dataset provided to comprise a match value, which specifies how probable it is for there to be a match between the position of the local radio-frequency coil established from the position information and the actual position of the local radio-frequency coil. This enables elements, in particular local radio-frequency coils and/or individual coil elements of a local radio-frequency coil, to be excluded from further use where a position cannot be uniquely determined. For example a high likelihood of a match between the position of the local radio-frequency coil and/or the coil elements of a local radio-frequency coil established from the position information and the actual position of the local radio-frequency coil and/or of the coil elements of a local radio-frequency coil is given a high match value and a low likelihood of a match between the position of the local radio-frequency coil and/or the coil elements of a local radio-frequency coil established from the position information and the actual position of the local radio-frequency coil and/or of the coil elements of a local radio-frequency coil is given a low match value.

In an advantageous development of the disclosed method for provision of a result dataset comprising position information of a local radio-frequency coil there can be provision for the result dataset to be provided for a number of local radio-frequency coils and/or a number of coil elements of a local radio-frequency coil at the same time. This enables position information to be determined and/or provided and/or carried out for a number of local radio-frequency coils and/or a number of coil elements of a local radio-frequency coil at the same time. Here the input data, magnetic resonance data in particular acquired by means of number of local radio-frequency coils and/or the number of coil elements of a local radio-frequency coil, is preferably passed at the same time to the trained function and/or the artificial neural network. In this case a dimension and/or a number of neurons of the trained function and/or of the artificial neural network can also increase according to the input data for a number of local radio-frequency coils and/or a number of coil elements of a local radio-frequency coil.

The disclosure is further based on a computer-implemented method for provision of a trained function, comprising:

receipt and/or determination of at least one training dataset of a local training radio-frequency coil, wherein the at least one training dataset comprises a training input dataset and a training result dataset and the training input dataset comprises magnetic resonance data of the local training radio-frequency coil, determination of a result dataset by application of the trained function to the training input dataset, adaptation of at least one parameter of the trained function based on a comparison of the training result dataset and the result dataset, and provision of the trained function.

The at least one training dataset, in particular the training input dataset of the at least one training dataset, has magnetic resonance data, which for example is acquired by means of the local training radio-frequency coil. Moreover it can also be that, for training the trained function and/or the artificial neural network, also instead of real magnetic resonance data, which is acquired by means of a local training radio-frequency coil, simulated magnetic resonance data is used. For example a simulated training dataset of this type, in particular a simulated magnetic resonance dataset, of the local training radio-frequency coil can be provided by means of a Bloch simulation and/or further simulation methods appearing sensible to the person skilled in the art.

Preferably, for a provision of the trained function and/or of an artificial neural network, training datasets, in particular training input datasets, of different local training radio-frequency coils and/or of different coil elements of a local training radio-frequency coil are made available. Moreover the training datasets, in particular the training input dataset, can comprise training data of coil combinations of a number of local training radio-frequency coils and/or of a number of coil elements of a local training radio-frequency coil.

Moreover, for the provision of the trained function and/or of an artificial neural network, training datasets, in particular training input datasets, can be made available, which have been acquired from different regions of the body by means of a local training radio-frequency coil and/or by coil elements of a local training radio-frequency coil. During a training phase, in which parameters and/or weights of the connections between two neurons of the trained function and/or of the artificial neural network are defined, supervised learning with backpropagation is proposed. The training of the trained function and/or of the artificial neural network should where possible take place individually for each coil type of a local radio-frequency coil, possibly also for widely-used coil combinations of local radio-frequency coils, in order to define suitable parameters and/or weights of neuron connections for each local radio-frequency coil or each widely-used coil combination of local radio-frequency coils. The optimization of the parameters and/or weights can then preferably occur with backpropagation.

The method for provision of a trained function advantageously enables an efficient method for provision of position information for a position recognition and/or a position determination and also an identification of local radio-frequency coils to be provided. In particular here the position recognition and/or the position determination and also the identification of local radio-frequency coils and/or of coil elements of a local radio-frequency coil can be done independently of a sensor system, such as for example cameras or sensors attached to the local radio-frequency coils, for detection and/or acquisition of the local radio-frequency coils and/or of coil elements of a local radio-frequency coil.

The advantages of the disclosed method for provision of a trained function essentially correspond to the advantages of the disclosed method for provision of a result dataset comprising position information, which has been set out above in detail. Features, advantages or alternate forms of aspect can likewise also be transferred to the other claimed subject matter and vice versa.

In an advantageous development of the disclosed method for provision of a trained function there can be provision for the trained function to be based on at least one training dataset with training data, wherein the training data comprises magnetic resonance data of different local training radio-frequency coils. In this way an efficient method for provision of position information for a position recognition and/or a position determination and also an identification of different local radio-frequency coils and/or of coil elements of a local radio-frequency coil can be provided.

In an advantageous development of the disclosed method for provision of a trained function there can be provision for the trained function to be based on at least one training dataset with training data, wherein the training data comprises magnetic resonance data with position information in at least one spatial direction. The training data here can comprise training data that is acquired by means of the local training radio-frequency coil or also simulated training data for a local training radio-frequency coil. The position information, in particular the spatial encoding, of the training data can be done in this case in one spatial direction or in a number of spatial directions. In this case separate training data, in particular a separate training spectrum, can be present for each spatial direction and/or location coordinate. Moreover it is also conceivable that here multidimensional training data, in particular a multidimensional training spectrum is present. The training data, in particular the training spectra, can be present already Fourier-transformed or also be present in the k-space coding. This aspect of the disclosure advantageously enables the trained function to be trained in respect of a positional accuracy. Moreover in this way a high level of positional accuracy in the determination of the position information of the local radio-frequency coils and/or of coil elements of a local radio-frequency coil can be achieved and thus a high level of efficiency of the disclosed method for provision of a result dataset comprising position information of a local radio-frequency coil and/or of coil elements of a local radio-frequency coil can be provided.

In an advantageous development of the disclosed method for provision of a trained function there can be provision for the trained function to be based on at least one training dataset with training data, wherein the training data comprises non-spatially encoded magnetic resonance data with different measurement frequencies. The training data here can comprise training data, which is acquired by means of the local training radio-frequency coil or also simulated training data for a local training radio-frequency coil. The training data in this case can be acquired or simulated with a measurement frequency, which comprises an average resonant frequency in a volume close to the center of a scanner unit of a magnetic resonance apparatus. Moreover the training data can also comprise measurement frequencies, which deviate from the resonant frequency. This enables the trained function and/or the artificial neural network to be trained especially efficiently in respect of local radio-frequency coils that are arranged and/or positioned outside a homogeneity region and/or linearity region of the scanner unit of the magnetic resonance apparatus.

In an advantageous development of the disclosed method for provision of a trained function there can be provision for the trained function to be based on at least one training dataset with training data, wherein the training data comprises a coil type and/or an examination region and/or a couch position and/or a position of the patient and/or anatomy information, in particular a size, of the patient. The training data here can comprise real training data or also simulated training data. This aspect of the method for provision of a trained function has the advantage that the trained function and/or the artificial neural network has a high sensitivity in respect of further coil parameters in the determination of a position of a local radio-frequency coil and/or of coil elements of a local radio-frequency coil.

In an advantageous development of the disclosed method for provision of a trained function there can be provision for the trained function to comprise at least two hidden layers and a maximum of ten hidden layers. Preferably the trained function comprises at least two hidden layers and a maximum of eight hidden layers. Especially advantageously the trained function comprises at least three hidden layers and a maximum of five hidden layers. The trained function and/or the artificial neural network in this case can also comprise a fully connected neural net, in which each neuron of one layer is linked to each neuron of the preceding layer and of the succeeding layer. In this way an especially reliable trained function for provision of position information can be made available.

In an advantageous development of the disclosed method for provision of a trained function there can be provision for the trained function to comprise at least one layer with LSTM (Long Short Term Memory) neurons. Here there can be a feedback between the individual neurons of different layers. This variant of the trained function and/or of the artificial neural network above all comprises an effective learning phase, in that with multilayer pure feed-forward networks in particular, i.e., with multilayer networks without feedback, the problem of parameters and/or weights of the front hidden layers only being inadequately optimized during the learning phase can be reduced and/or prevented.

In an advantageous development of the disclosed method for provision of a trained function there can be provision for the trained function to comprise at least one hidden layer embodied as a drop-out layer. Such drop-out layers comprise a regularization method in order to prevent and/or to reduce an overfitting of the trained function and/or of the artificial neural network. Here randomly selected individual neurons in the drop-out layers are deactivated during training of the trained function and/or of the artificial neural network and not taken into account for the next computing step.

The disclosure is furthermore based on a provision system for provision of a result dataset, comprising an interface and a processor unit,
wherein the interface and/or the processor unit are embodied for provision of input data,
wherein the processor unit is embodied for determination of a result dataset by application of a trained function to the input data comprising magnetic resonance data of the local radio-frequency coil, wherein the result dataset comprises position information of the local radio-frequency coil, and
wherein the interface is furthermore embodied for provision of the result dataset.

The processor unit comprises at least one processing module and/or a processor, wherein the processor unit is embodied for determination of a result dataset by application of the trained function and/or of the artificial neural network to the input data comprising magnetic resonance data. In this way the processor unit is embodied in particular to carry out computer-readable instructions for determination of a result dataset by application of a trained function and/or of the artificial neural network to the input data comprising the magnetic resonance data. In particular the processor unit comprises a memory unit, wherein computer-readable information is stored on the memory unit, wherein the processor unit is embodied to load the computer-readable information from the memory unit and to execute the computer-readable information. In this way the disclosed processor unit is embodied to carry out a determination of a result dataset by application of a trained function and/or of the artificial neural network to the input data comprising magnetic resonance data.

The components of the processor unit can be embodied for the most part in the form of software components. Basically however some of these components, in particular when it is a matter of fast computations, can be realized in the form of software-supported hardware components, for example FPGAs or the like. In particular, for tasks and/or applications for machine learning, the components of the processor unit can comprise specialized and/or optimized components, such as for example a TPU (Tensor Processing Unit) and/or an NPU (Neural Processing Unit), with which use within the framework of machine learning can be carried out in an accelerated manner. Likewise the interfaces needed, for example when it is only a matter of receiving data from other software components, can be embodied as software interfaces. They can however also be embodied as interfaces constructed from hardware, which are activated by suitable software. Naturally it is also conceivable for a number of the said components to be realized grouped together in the form of one individual software component or software-supported hardware component. The processor unit preferably comprises the trained function and/or the artificial neural network.

By means of the provision unit an efficient method can advantageously be provided for provision of position information about a position recognition and/or a position determination and also an identification of local radio-frequency coils and/or of individual coil elements of a local radio-frequency coil.

The advantages of the disclosed provision system essentially correspond to the advantages of the disclosed method for provision of a result dataset comprising position information, which have been set out in detail above. Features, advantages or alternate forms of aspect mentioned here can likewise be transferred to the other claimed subject matter and vice versa.

The disclosure is furthermore based on a magnetic resonance apparatus comprising a provision system, wherein the provision system is embodied for provision of a result dataset and comprises an interface and a processor unit,
wherein the interface and/or the processor unit are embodied for provision of input data,
wherein the processor unit is embodied for determination of a result dataset by application of a trained function to the input data comprising magnetic resonance data of the local radio-frequency coil, wherein the result dataset comprises position information of the local radio-frequency coil, and
wherein the interface is furthermore embodied for provision of the result dataset.

The magnetic resonance apparatus preferably comprises a medical and/or diagnostic magnetic resonance apparatus, which is designed and/or embodied to acquire medical and/or diagnostic image data, in particular medical and/or diagnostic magnetic resonance image data, of a patient. The magnetic resonance apparatus preferably comprises a scanner unit. The scanner unit of the magnetic resonance apparatus preferably comprises a detector unit, in particular a magnet unit, for acquisition of the medical and/or diagnostic image data. Preferably the scanner unit here, in particular the magnet unit, comprises a basic magnet, gradient coil unit and a radio-frequency antenna unit. The radio-frequency antenna unit is arranged permanently within the scanner unit and is designed and/or embodied to emit an excitation pulse. Furthermore the magnetic resonance apparatus has at least one local radio-frequency coil, which is embodied for receiving a magnetic resonance signal. To this end the local radio-frequency coil is arranged and/or placed around the region of the patient to be examined. Preferably the local radio-frequency coils are specifically designed for one area of a patient to be examined, such as for example a radio-frequency head coil or a radio-frequency knee coil etc.

The basic magnet is embodied to create a homogenous basic magnetic field. In particular the basic magnet is embodied to create a strong and constant basic magnetic field. The homogeneous basic magnetic field is preferably arranged and/or to be found within a patient accommodation area of the magnetic resonance apparatus. The patient accommodation area is designed and/or embodied to accommodate the patient, in particular the region of the patient to be examined, for a medical magnetic resonance examination. For example the patient accommodation area is embodied in a cylindrical shape and/or surrounded in a cylindrical shape by the scanner unit, in particular the magnetic unit for this purpose.

Arranged within the patient accommodation area is preferably a Field of View (FOV) and/or an isocenter of the magnetic resonance apparatus. The FOV preferably comprises a detection area of the magnetic resonance apparatus, within which the conditions for a detection of medical image data, in particular magnetic resonance image data, within the patient accommodation area are present, such as for example a homogeneous basic magnetic field. The isocenter of the magnetic resonance apparatus preferably comprises the area and/or point within the magnetic resonance apparatus that has the optimal and/or ideal conditions for the acquisition of medical image data. In particular the isocenter comprises the most homogeneous magnetic field area within the magnetic resonance apparatus.

By means of the magnetic resonance apparatus an efficient method for a provision of position information for a position recognition and/or a position determination as well as an identification of local radio-frequency coils is able to be provided.

The advantages of the disclosed magnetic resonance apparatus essentially correspond to the advantages of the disclosed method for provision of a result dataset comprising position information, which have been set out in detail above. Features, advantages or alternate forms of aspect mentioned here can likewise be transferred to the other claimed subject matter and vice versa.

The disclosure is furthermore based on a computer program product with a computer program, which is able to be loaded directly into a memory of a provision system, with program sections for carrying out all steps of the method for provision of a result dataset comprising position information of a local radio-frequency coil when the program sections are executed by the provision system; and/or which is able to be loaded directly into a training memory of a training system, with program sections for carrying out all steps of the method for provision of a trained function when the program sections are executed by the training system. In this case the computer program may possibly need program means, e.g. libraries and auxiliary function for realizing the corresponding forms of aspect of the method. The computer program in this case can comprise software with a source code that still has to be compiled and linked or only has to be interpreted, or executable software code, which still has to be loaded into a corresponding processor unit to execute it.

The disclosed computer program product is able to be loaded directly into a memory of a programmable processor unit and has program code means for carrying out an disclosed method when the computer program product is executed in the processor unit. The computer program product can be a computer program or comprise a computer program. This enables the disclosed method to be carried out quickly, identically repeatably and robustly. The computer program product is configured in such a way that it can carry out the disclosed method steps by means of the processor unit. The processor unit in this case must have the prerequisites in each case, such as for example a corresponding main memory, a corresponding graphics card or a corresponding logic unit, so that the respective method steps can be carried out efficiently. The computer program product is for example stored on a computer-readable medium or held on a network or server, from where it can be loaded into the processor of a local processor unit, which can be directly connected to the magnetic resonance apparatus or be embodied as part of it. Furthermore control information of the computer program product can be stored on an electronically-readable data medium. The control information of the electronically-readable data medium can be embodied in such a way that, when the data medium is used in a processing unit, it carries out an disclosed method. In this way the computer program product can also represent the electronically-readable data medium. Examples of electronically-readable data media are a DVD, a magnetic tape, a hard disk or a USB stick, on which electronically-readable control information, in particular software (cf. above), is stored. In this way the disclosure can also be based on the said computer-readable medium and/or on the said electronically-readable data medium.

The disclosure is furthermore based on a computer-readable memory medium, on which program sections able to be read and executed by a provision system are stored in order to carry out all steps of the method for provision of a result dataset comprising position information of a local radio-frequency coil when the program sections are executed by the provision system; and/or on which program sections able to be read and executed by a training system are stored in order to carry out all steps of the method for provision of a trained function when the program sections are executed by the training system.

BRIEF DESCRIPTION OF THE DRAWINGS

Further advantages, features and details of the disclosure emerge from the exemplary aspects described below and also with the aid of the drawings. In the figures:

FIG. 6 shows a magnetic resonance apparatus with a provision system in a schematic diagram.

DETAILED DESCRIPTION

Figure 1:
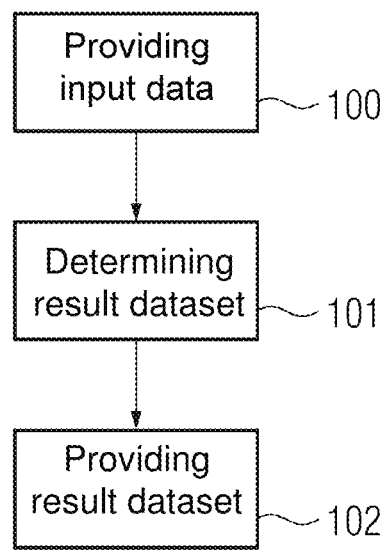
FIG. 1 shows a method for provision of a result dataset comprising position information of a local radio-frequency coil.

Shown in FIG. 1 is a method for provision of a result dataset comprising position information of a local radio-frequency coil 600. In a first method step 100 there is a provision of input data, wherein the input data at least comprises magnetic resonance data, which is acquired by means of the local radio-frequency coil 600. The input data is preferably provided by means of a provision system 400, as is described in the remarks relating to FIG. 4 below. In particular the input data comprising magnetic resonance data acquired at least by means of the local radio-frequency antenna 600 is provided by means of an interface 401, in particular by means of an interface 401 of the provision system 400. The input data has been acquired before the beginning of the method by means of the local radio-frequency coil 600 and is transferred from the local radio-frequency coil 600 to the provision system 400.

In this case the input data can also comprise magnetic resonance data, which is acquired by means of a local radio-frequency coil 600 or also by means of two or more local radio-frequency coils 600 and/or also by means of two or more coil elements of a local radio-frequency coil 600. The input data can moreover also comprise additional information, such as for example which local radio-frequency coil 600 and/or which coil elements of the local radio-frequency coil 600 have been used for the acquisition of magnetic resonance data included in the input data. Moreover the input data can also comprise additional information, such as for example a region to be examined of the patient and/or a couch position and/or position information of the patient and/or anatomy information, in particular size information, of the patient and/or further information appearing sensible to the person skilled in the art.

In this first method step 100 the input data provided here can comprise magnetic resonance data acquired by means of the local radio-frequency coil 600, wherein the magnetic resonance data comprises position information in at least one spatial direction. The position information of the magnetic resonance data in this case can preferably comprise a spatial encoding of the acquired magnetic resonance data. For example the magnetic resonance data with position information, in particular spatial encoding, can be acquired by means of a spin echo measurement and/or a gradient echo measurement. The position information, in particular the spatial encoding, of the magnetic resonance data in this case can comprise one spatial direction or a number of spatial directions. The magnetic resonance data with position information, in particular a spatial encoding, in a number of spatial directions and/or a number of spatial coordinates can be present for each spatial direction and/or each spatial coordinate as separate magnetic resonance data, in particular as a separate spectrum. As an alternative or in addition it is also conceivable for the magnetic resonance data with position information, in particular a spatial encoding, to be present in a number of spatial directions and/or a number of spatial coordinates as multidimensional magnetic resonance data, in particular as a multidimensional spectrum. The magnetic resonance data, in particular the spectra, can further be present already Fourier-transformed or also in the k-space encoding.

As an alternative or in addition, in this first method step, the input data provided here can comprise magnetic resonance data acquired by means of the local radio-frequency coil 600, wherein the magnetic resonance data of the local radio-frequency coil 600 is normalized in relation to magnetic resonance data of a homogeneous radio-frequency coil. The homogeneous radio-frequency coil preferably comprises a body coil. In particular here a receive profile of acquired magnetic resonance data and/or signals of the body coil is more homogeneous than for example a receive profile of acquired magnetic resonance data and/or signals of a knee coil and/or further local radio-frequency coils. A normalization of the acquired magnetic resonance data can for example comprise a division of the magnetic resonance data acquired by means of the local radio-frequency coil 600, in particular magnetic resonance data with a spatial encoding, by the magnetic resonance data and/or signals acquired with the homogeneous radio-frequency coil, in particular the body coil, for each spatial point. The magnetic resonance data and/or signals of the homogeneous radio-frequency coil in this case can also be acquired separately from the acquisition of the magnetic resonance data by means of the local radio-frequency coil 600.

As an alternative or in addition, in this first method step the input data provided here can comprise magnetic resonance data acquired by the local radio-frequency coil 600, wherein the magnetic resonance data comprises non-spatially-encoded magnetic resonance data with different measurement frequencies. The magnetic resonance data can comprise in this case with a measurement frequency, which comprises an average resonant frequency in the volume close to the center of a scanner unit of a magnetic resonance apparatus. Moreover the magnetic resonance data can also comprise measurement frequencies, which deviate from the average resonant frequency. Through this in particular local radio-frequency coils 600 and/or coil elements of a local radio-frequency coil 600 can be identified and/or position information reliably acquired from local radio-frequency coils 600 and/or coil elements of a local radio-frequency coil 600, with said local radio-frequency coils 600 and/or coil elements of a local radio-frequency coil 600 preferably being arranged and/or positioned outside of a homogeneity area and/or linearity area of a scanner unit 602 of a magnetic resonance apparatus 601.

Moreover it can also be that the input data provided, in particular magnetic resonance data acquired by means of the local radio-frequency coil 600, is already pre-processed, such as for example by smoothing and/or filtering of the input data.

Subsequently, in a further, second method step 101, there is a determination of a result dataset by application of a trained function 300 to the input data, wherein the result dataset comprises position information for determining the position of the local radio-frequency coil 600. The result dataset is preferably determined by means of a determination unit and/or a processing unit 402, in particular by means of a determination unit and/or a processing unit 402 of the provision system 400.

The trained function 300 preferably comprises an artificial neural network. In this way the provision of a result dataset comprising position information of a local radio-frequency coil 600 is based in particular on a machine learning process, which is based on the artificial neural network. An artificial neural network (ANN) is in particular a network of artificial neurons emulated in a computer program. The artificial neural network in this case is typically based on a networking of a number of artificial neurons. The artificial neurons in this case are typically arranged on different layers. Usually the artificial neural network comprises an input layer 301 and an output layer 303, of which the neuron output is visible as the only layer of the artificial neural network. Layers lying between the input layer and the output layer are typically referred to as hidden layers 302. Further information about the trained function 300 and/or of the artificial neural network is provided below in the explanation of FIG. 3.

The trained function 300 and/or the artificial neural network has in particular already been suitably trained in advance for the determination of position information for determining the position of the local radio-frequency coil 600 with the aid of the acquired magnetic resonance data. Training datasets are used in particular in this case for the training of the trained function 300 and/or of the artificial neural network, in which for example a signal intensity of the magnetic resonance data acquired by means of the local radio-frequency coil is assigned to a position and/or position information of the local radio-frequency coil. The medical training datasets in this case are typically acquired from training persons and/or training radio-frequency coils different from the patient.

The result dataset preferably comprises the position information for determining the position of the local radio-frequency coil 600 and/or a position of coil elements of a local radio-frequency coil 600. The result dataset in this case can also directly comprise the position of the local radio-frequency coil 600 and/or the position of coil elements of a local radio-frequency coil 600. Moreover the result dataset can also comprise further information relating to the position of the local radio-frequency coil 600 and/or relating to the position of coil elements of a local radio-frequency coil 600. For example the result dataset here can also comprise information and/or a match value, which specify how likely it is that there is a match between the position of the local radio-frequency coil 600 and/or of coil elements of a local radio-frequency coil 600 established from the position information and the actual position of the local radio-frequency coil 600 and/or of coil elements of a local radio-frequency coil 600. Moreover it can also be that the result dataset also contains information that no local radio-frequency coil 600 and/or no coil element of a local radio-frequency coil 600 could be determined or that a position could not be determined for any local radio-frequency coil 600 and/or any coil element of a local radio-frequency coil 600. In such a case the position information can assume the value "0" for example.

In a further, third method step 102 following on from this there is a provision of the result dataset. The result dataset is preferably provided by means of the provision system 400, in particular by means of the interface 401 of the provision system 400. In this case, in this third method step 102, the result dataset can also be provided for a number of local radio-frequency coils 600 and/or for a number of coil elements of a local radio-frequency coil 600 at the same time. Preferably the input data provided here also comprises the information as to the local radio-frequency coils 600 and/or coil elements of a local radio-frequency coil 600 for which magnetic resonance data is available. In this case, when different combinations of local radio-frequency coils 600 and/or of coil elements of a local radio-frequency coil 600 are used, different parameterizations of the trained function 300 and/or of the artificial neural network can be used.

If for example for a measurement the local radio-frequency coils 600 of type A and type B are used together, this data can be passed together in the first method step 101 to the trained function 300 and/or to the artificial neural network. Thus a different parameterization of the trained function 300 and/or of the artificial neural network is used than if local radio-frequency coils 600 of type A and C or just one local radio-frequency coil 600 of type A were used on its own.

Figure 2:
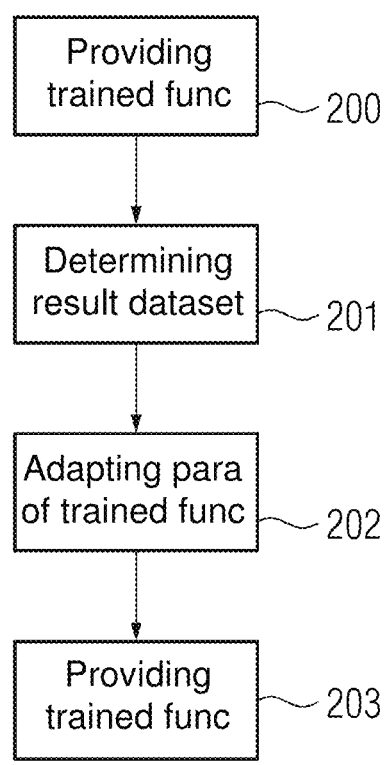
FIG. 2 shows a method for provision of a trained function.

Shown in FIG. 2 is a computer-implemented method for provision of the trained function 300, wherein the trained function 300 is embodied to determine a result dataset with the aid of input data. The trained function 300 is preferably provided by means of a training system 500.

In a first method step 200 of the method for provision of the trained function 300 there is a receipt or determination of at least one training dataset of a local training radio-frequency coil, wherein the at least one training dataset comprises a training input dataset and a training result dataset and the training input dataset comprises magnetic resonance data of the local training radio-frequency coil. The at least one training dataset, in particular the training input dataset of the at least one training dataset, in particular has magnetic resonance data, which is acquired for example by means of the local training radio-frequency coil. Moreover it can also be that for training of the trained function 300 and/or of the artificial neural network also, instead of real magnetic resonance data, simulated magnetic resonance data is used. For example a dataset simulated in this way, in particular a simulated magnetic resonance dataset, of a local training radio-frequency coil can be provided by means of a Bloch simulation and/or by further simulation methods appearing sensible to the person skilled in the art.

Figure 5:
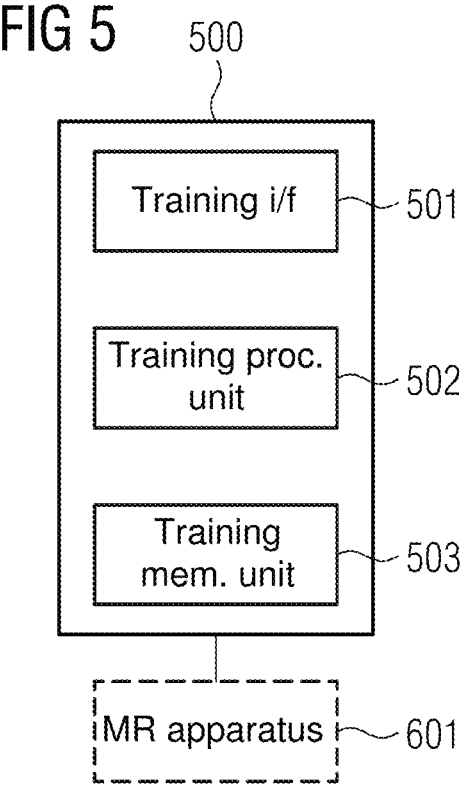
FIG. 5 a training system in a schematic diagram.

The at least one training dataset is received or determined in particular by means of a training processing unit 502 and/or a training interface 501, in particular by means of the training processing unit 502 and/or the training interface 501 of the training system 500 (see FIG. 5). The result dataset is determined and the parameters of the trained function 300 and/or of the artificial neural network adapted in particular by means of the training processing unit 502 of the training system 500. The trained function 300 and/or the artificial neural network are provided in particular by means of the training interface 501 of the training system 500.

Preferably, for a provision of the trained function 300 and/or of an artificial neural network, training datasets, in particular the training input datasets and training result datasets of different local training radio-frequency coils and/or of different coil elements of a local training radio-frequency coil are made available. Moreover the training datasets, in particular training input datasets and training result datasets, comprise training data of coil combinations of a number of local training radio-frequency coils and/or of a number of coil elements of a local training radio-frequency coil. Moreover, for the provision of the trained function 300 and/or of an artificial neural network, training datasets, in particular training input datasets and training result datasets, can be made available, which were acquired from different regions of the body by means of a local training radio-frequency coil and/or by coil elements of a local training radio-frequency coil.

In this first method step 200 the at least one training dataset, in particular the training input dataset of the at least one training dataset, can comprise training data, wherein the training data comprises magnetic resonance data with position information in at least one spatial direction. The position information, in particular the spatial encoding, of the training data can be undertaken in this case in one spatial direction or in a number of spatial directions. In this case, for each spatial direction and/or spatial coordinate, separate training data, in particular a separate training spectrum, can be present. Moreover it is also conceivable for multidimensional training data, in particular a multidimensional training spectrum, to be present here. The training data, in particular the training spectra, can further be present here already Fourier-transformed or also in the k-space encoding.

Furthermore, in this first method step 200, the at least one training dataset, in particular the training input dataset of the at least one training dataset, can comprise training data, wherein the training data comprises non spatially-encoded magnetic resonance data with different measurement frequencies. The training data can in this case comprise with a measurement frequency, which comprises an average resonant frequency in the volume close to the center of the scanner unit 602 of the magnetic resonance apparatus 600. Moreover the training data can also comprise measurement frequencies, which deviate from the average resonant frequency.

Furthermore, in this first method step 200, the at least one training dataset, in particular the training input dataset of the at least one training dataset, can comprise training data, wherein the training data comprises further coil information, in particular a coil type and/or an examination region and/or a couch position. Moreover in this first method step 200, the training data can also comprise a position and/or position information of the patient and/or anatomy information of the patient. The anatomy information can for example comprise a size and/or extent of the patient.

Figure 3:
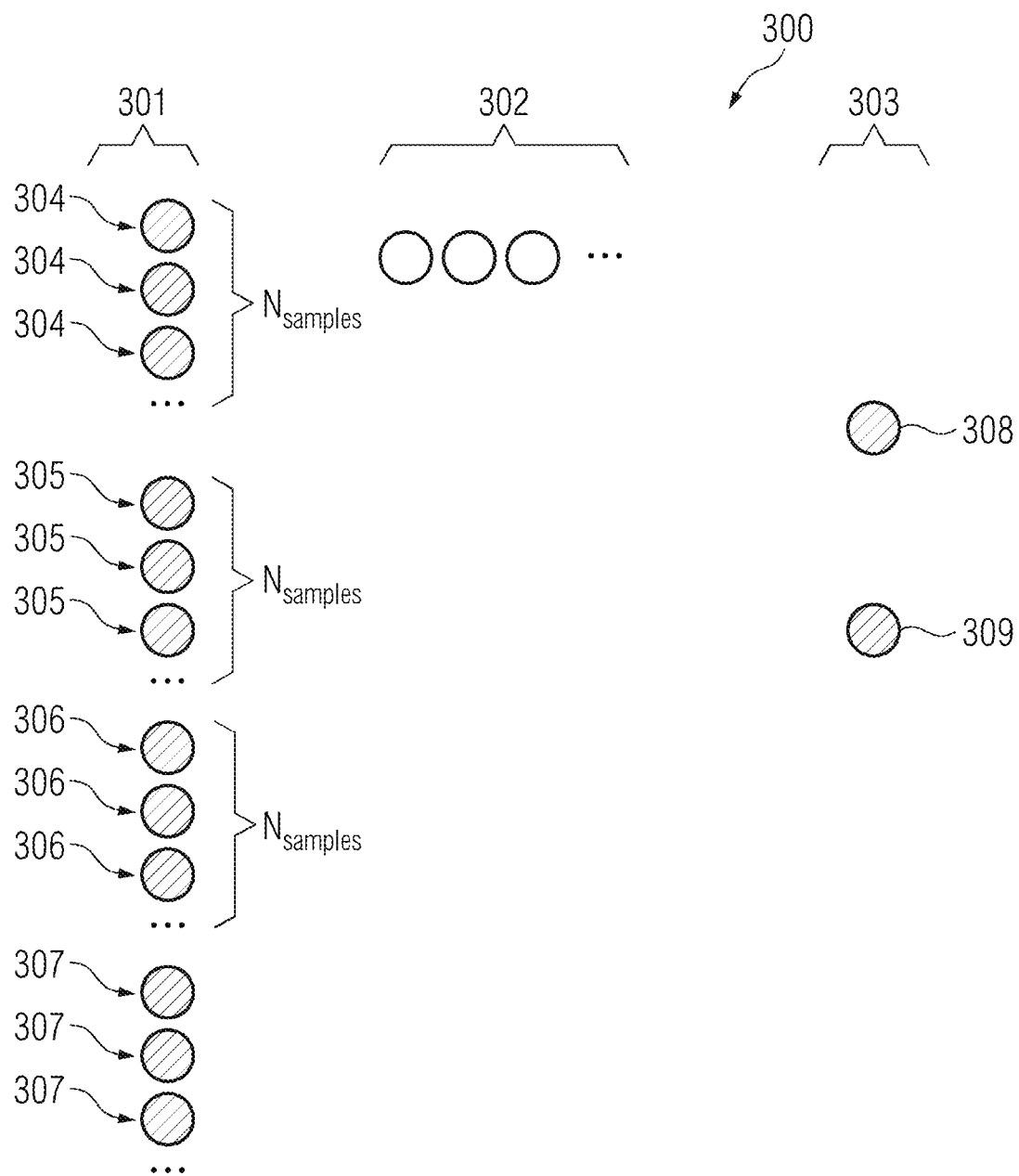
FIG. 3 shows a trained function in a schematic diagram.

In a subsequent second method step 201 of the method for provision of the trained function 300 there is a determination of a result dataset by application of the trained function 300 to at least one training dataset, in particular to the training input dataset. The trained function 300 and/or the artificial neural network preferably comprises an input layer, a number of hidden layers and an output layer, as is shown in FIG. 3. Preferably the trained function 300 and/or the artificial neural network comprises at least two hidden layers and a maximum of ten hidden layers. Preferably the trained function 300 and/or the artificial neural network comprises at least two hidden layers and a maximum of eight hidden layers. Especially advantageously the trained function 300 and/or the artificial neural network comprises at least three hidden layers and a maximum of five hidden layers.

The trained function 300 and/or the artificial neural network can also comprise a fully connected neural net in this case, in which each neuron of a layer is connected to each neuron of the preceding layer and of the succeeding layer. Moreover the trained function 300 and/or the artificial neural network can comprise at least one layer with LSTM neurons (Long Short Term Memory neurons). Here there can be feedback between the neurons of different layers. This variant of the trained function 300 and/or of the artificial neural network above all comprises an effective learning phase, in that in multilayer pure feed-forward networks in particular, i.e. in multilayer networks without feedback, the problem of parameters and/or weights of the front hidden layers only being inadequately optimized during the learning phase, can be reduced and/or prevented.

The trained function 300 and/or the artificial neural network can comprise at least one hidden layer embodied as a drop-out layer. Such drop-out layers comprise a regularization method in order to reduce and/or to prevent an overfitting of the trained function 300 and/or of the artificial neural network. Here, during the training of the trained function 300 and/or of the artificial neural network, individual neurons in the drop-out layers chosen at random are deactivated and not taken into account for the next computation step.

In a subsequent third method step 202 of the method for provision of the trained function 300, at least one parameter of the trained function 300 is adapted based on a comparison of the training result dataset of the at least one training dataset and the result dataset. In this third method step 202 parameters and/or weights of the links between two neurons of the trained function 300 and/or of the artificial neural network are defined. In particular the parameters and/or weights of the links between two neurons of the trained function 300 and/or of the artificial neural network are defined by means of supervised learning with back propagation. The parameters and/or weights are thus optimized by means of backpropagation. The training of the trained function 300 and/or of the artificial neural network should take place individually where possible for each coil type of a local radio-frequency coil, possibly also for widely-used coil combinations of local radio-frequency coils in order to define suitable parameters and/or weights or neuron connections for each local radio-frequency coil or for each widely-used coil combination of local radio-frequency coils.

In a subsequent fourth method step 203 of the method for provision of the trained function 300 the trained function 300 is provided. The trained function 300 and/or the artificial neural network are preferably provided by means of the training interface 501 of the training system 500. The provision can in particular comprise a storage, display and/or transmission of the trained function 300 and/or of the artificial neural network. In particular, the trained function 300 and/or the artificial neural network can be transmitted to the provision system 400 or used in a method for provision of a result dataset in accordance with the disclosure and its aspects.

Shown in FIG. 3 in greater detail is the trained function 300 and/or the artificial neural network. The trained function 300 and/or the artificial neural network comprises an input layer 301, a number of hidden layers 302 and an output layer 303.

The input layer 301 in this case can comprise input data 304, which comprises magnetic resonance data with position information in at least one spatial direction. Furthermore the input layer 301 can comprise input data 305, which comprises non-spatially-encoded magnetic resonance data, which comprises a measurement frequency that is the same as the resonant frequency. The input layer 301 can furthermore comprise input data 306 with non-spatially-encoded magnetic resonance data, which comprises a measurement frequency that is different from the resonant frequency. Furthermore the input layer 301 has further input data 307, which comprises additional coil information.

The hidden layers 302 preferably comprise at least two hidden layers 302 and a maximum of ten hidden layers 302. Preferably the trained function comprises at least two hidden layers 302 and a maximum of eight hidden layers 302. Especially advantageously the trained function comprises at least three hidden layers 302 and a maximum of five hidden layers 302. The hidden layers are only shown schematically in FIG. 3 and do not reproduce the links of the individual neurons between the individual layers as described above.

The output layer 303 comprises the result dataset provided. This result dataset comprises the position information 308 and the match value 309.

Figure 4:
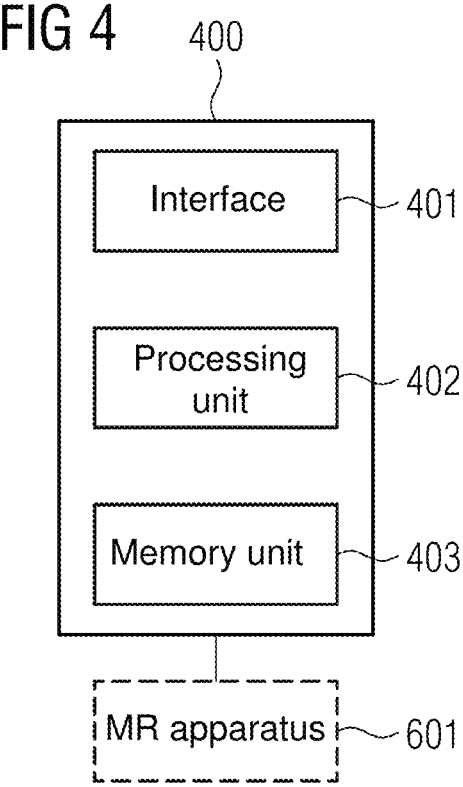
FIG. 4 shows a provision system in a schematic diagram.

Shown schematically in FIG. 4 is the provision system 400. The provision system 400 shown is embodied to carry out a disclosed method for provision of a result dataset comprising position information of a local radio-frequency coil 600 and/or of coil elements of a local radio-frequency coil 300. The provision system 400 comprises an interface 401, a processor unit 402 and a memory unit 403.

The provision system 400 can in particular involve a computer, a microcontroller or an integrated circuit. As an alternative the provision system 400 can involve a real or virtual group of computers (a real group is a cluster and a virtual group is a cloud). The provision system 400 can also be embodied as a virtual system, which is executed on a real computer or on a real or virtual group of computers (the technical term is virtualization).

The interface 401 can involve a hardware interface or software interface (for example PCI bus, USB or Firewire). The processor unit 402 can have hardware elements or software elements, for example a microprocessor or what is known as an FPGA (acronym for Field Programmable Gate Array). Moreover the processor unit 402 can comprise components that are specialized and/or optimized for tasks and/or applications for machine learning, such as for example a GPU (Global Processing Unit) and/or a TPU (Tensor Processing Unit) and/or an NPU (Neural Processing Unit), with the use of which as part of machine learning the process can be carried out more quickly. The memory unit 403 can be realized as non-permanent working memory (Random Access Memory, abbreviated to RAM) or as permanent mass memory (hard disk, USB stick, SD card, Solid State Disk). The interface 401 can in particular comprise a number of sub interfaces, which carry out different steps of the respective method. The processor unit 402 can in particular comprise a number of sub processor units, which carry out different steps of the respective method.

Shown schematically in FIG. 5 is the training system 500. The training system 500 shown is embodied to carry out an disclosed method for provision of a result dataset. The training system 500 comprises a training interface 501, a training processing unit 502 and a training memory unit 503.

The training system 500 can in particular involve a computer, a microcontroller or an integrated circuit. As an alternative the training system 500 can involve a real or virtual group of computers (a real group is a cluster and a virtual group is a cloud). The training system 500 can also be embodied as a virtual system, which is executed on a real computer or on a real or virtual group of computers (the technical term is virtualization).

The training interface 401 can involve a hardware interface or software interface (for example PCI bus, USB or Firewire). The training processor unit 402 can have hardware elements or software elements, for example a microprocessor or what is known as an FPGA (acronym for Field Programmable Gate Array). Moreover the training processor unit 402 can comprise components that are specialized and/or optimized for tasks and/or applications for machine learning, such as for example a GPU (Global Processing Unit) and/or a TPU (Tensor Processing Unit) and/or an NPU (Neural Processing Unit), with the use of which as part of machine learning the process can be carried out more quickly. The training memory unit 403 can be realized as non-permanent working memory (Random Access Memory, abbreviated to RAM) or as permanent mass memory (hard disk, USB stick, SD card, Solid State Disk). The training interface 501 can in particular comprise a number of sub interfaces, which carry out different steps of the respective method. The training processor unit 402 can in particular comprise a number of sub processor units, which carry out different steps of the respective method.

Shown schematically in FIG. 6 is the magnetic resonance apparatus 601. The magnetic resonance apparatus 601 comprises a scanner unit 602 formed by a magnet unit. Moreover the magnetic resonance apparatus 601 has a patient accommodation area 603 for accommodating a patient 604. In the present exemplary aspect the patient accommodation area 603 is embodied in a cylindrical shape and is surrounded in a circumferential direction in a cylindrical shape by the scanner unit 602, in particular by the magnet unit. Basically however an aspect of the patient accommodation area 603 differing therefrom is always conceivable. The patient 604 can be pushed and/or moved by means of a patient accommodation apparatus 605 of the magnetic resonance apparatus 601 into the patient accommodation area 603. For this purpose the patient accommodation apparatus 605 has a patient couch 606 embodied movably within the patient accommodation area 603. In particular the patient couch 606 is movably supported here in the direction of a longitudinal extent of the patient accommodation area 603 and/or in the z-direction.

The scanner unit 602, in particular the magnet unit, comprises a superconducting basic magnet 607 for creating a strong and in particular constant basic magnetic field 608. Furthermore the scanner unit 602, in particular the magnet unit, has a gradient coil unit 609 for creation of magnetic field gradients, which are used for spatial encoding during imaging. The gradient coil unit 609 is controlled by means of a gradient control unit 610 of the magnetic resonance apparatus 601. The scanner unit 602, in particular the magnet unit, furthermore comprises a radio-frequency antenna unit 611 for exciting a polarization, which is set up in the basic magnetic field 608 created by the basic magnet 607. The radio-frequency antenna unit 611 is controlled by a radio-frequency antenna control unit 612 of magnetic resonance apparatus 601 and radiates radio-frequency magnetic resonance sequences into the patient accommodation area 603 of the magnetic resonance apparatus 601.

The magnetic resonance apparatus 601 furthermore comprises a local radio-frequency coil 600 for receiving a magnetic resonance signal. To this end the local radio-frequency coil 600 is arranged around a region of the patient 604 to be examined. Preferably the local radio-frequency coils 600 are specifically designed for one examination area of the patient, such as for example radio-frequency head coil to acquire magnetic resonance signals during an examination of the head or a radio-frequency knee coil to acquire magnetic resonance signals during an examination of the knee etc.

For control of the basic magnet 607, of the gradient control unit 610 and for control of the radio-frequency antenna control unit 612 the magnetic resonance apparatus 601 has a system control unit 613. The system control unit 613 centrally controls the magnetic resonance apparatus 601, such as for example the carrying out of a predetermined imaging gradient echo sequence. Moreover the system control unit 613 comprises an evaluation unit not shown in any greater detail for an evaluation of medical image data, which is acquired during the magnetic resonance examination.

The magnetic resonance apparatus 601 furthermore comprises the provision system 400, which is connected to the system control unit 613. As an alternative to the exemplary aspect shown it is also possible for the provision system 400 to be embodied as part of the system control unit 613.

The magnetic resonance apparatus 601 furthermore comprises a user interface 614, which is connected to the system control unit 613. Control information such as for example imaging parameters, as well as reconstructed magnetic resonance images, can be displayed on a display unit 615, for example on at least one monitor, of the user interface 614 for medical operating personnel. The user interface 614 furthermore has an input unit 616, by means of which information and/or parameters can be entered during a measurement process by the medical operating personnel.

The magnetic resonance apparatus 601 shown can of course comprise further components that magnetic resonance apparatuses 601 usually have. The general way in which a magnetic resonance apparatus 601 functions is moreover known to the person skilled in the art, so that a more detailed description of the further components will be dispensed with here.

Although the disclosure has been illustrated and described in detail by the preferred exemplary aspects, the disclosure is not restricted by the disclosed examples and other variations can be derived herefrom by the person skilled in the art, without departing from the scope of protection of the disclosure.

The invention claimed is:

1. A computer-implemented method for providing a result dataset including position information of a local radio-frequency coil, the method comprising:
   providing input data including input magnetic resonance data, which is acquired by means of the local radio-frequency coil,
   wherein the input magnetic resonance data is normalized with respect to magnetic resonance data acquired via a radio-frequency body coil by performing a division of magnetic resonance data acquired via the local radio-frequency coil by magnetic resonance data acquired via the radio-frequency body coil for each spatial point, and wherein a receive profile of the magnetic resonance data acquired via the radio-frequency body coil is more homogenous than a receive profile of the magnetic resonance data acquired via the local radio-frequency coil;

determining a result dataset by applying a trained function to the input data, the trained function comprising an artificial neural network (ANN), wherein the result dataset includes position information for determining the position of the local radio-frequency coil; and providing the result dataset.

2. The method of claim 1, wherein the input magnetic resonance data includes position information in a spatial direction.

3. The method of claim 1, wherein the input magnetic resonance data includes non-spatially encoded magnetic resonance data with different measurement frequencies.

4. The method of claim 1, wherein the input data includes a further item of coil information of the local radio-frequency coil.

5. The method of claim 1, wherein the result dataset includes a match value, which specifies how likely there is to be a match between the position of the local radio-frequency coil established from the position information and an actual position of the local radio-frequency coil.

6. The method of claim 1, wherein the result dataset is provided for a number of local radio-frequency coils and/or for a number of coil elements of a local radio-frequency coil at the same time.

7. A non-transitory computer-readable memory medium on which program sections which are readable and executable by a provision system are stored, for carrying out the method of claim 1 when the program sections are executed by the provision system.

8. The method of claim 1, wherein the input data comprises magnetic resonance data acquired from different regions of a patient body via respective local training radio-frequency coils.

9. The method of claim 1, wherein the magnetic resonance data of the radio-frequency body coil is acquired separately from the magnetic resonance data acquired via the local radio-frequency coil.

10. A computer-implemented method for providing a trained function, comprising:

receiving or determining a training dataset of a local training radio-frequency coil, wherein the training dataset includes a training input dataset and a training result dataset, and the training input dataset includes input magnetic resonance data of the local training radio-frequency coil, wherein the input magnetic resonance data is normalized with respect to magnetic resonance data acquired via a radio-frequency body coil by performing a division of magnetic resonance data acquired via the local radio-frequency coil by magnetic resonance data acquired via the radio-frequency body coil for each spatial point, and wherein a receive profile of the magnetic resonance data acquired via the radio-frequency body coil is more homogenous than a receive profile of the magnetic resonance data acquired via the local radio-frequency coil;

determining a result dataset by applying the trained function to the training input dataset, the trained function comprising an artificial neural network (ANN);

adapting a parameter of the trained function based on a comparison between the training result dataset and the result dataset; and providing the trained function.

11. The method of claim 10, wherein the trained function is based on the training dataset with training data, and the training data comprises the input magnetic resonance data acquired via different local training radio-frequency coils.

12. The method of claim 10, wherein the trained function is based the training dataset with training data, and the training data comprises the input magnetic resonance data with position information in a spatial direction.

13. The method of claim 10, wherein the trained function is based on the training dataset with training data, and the training data comprises non-spatially-encoded magnetic resonance data with different measurement frequencies.

14. The method of claim 10, wherein the trained function is based on the training dataset with training data, and the training data comprises a coil type and/or an examination region and/or a couch position and/or a position of the patient and/or anatomy information of the patient.

15. The method of claim 10, wherein the trained function comprises at least two hidden layers and a maximum of ten hidden layers.

16. The method of claim 10, wherein the trained function comprises a layer with LSTM (Long Short Term Memory) neurons.

17. The method of claim 10, wherein the trained function comprises a hidden layer embodied as a drop-out layer.

18. A non-transitory computer-readable memory medium on which program sections which are readable and executable by a training system are stored, for carrying out the method of claim 10 when the program sections are executed by the training system.

19. A provision system for provision of a result dataset, comprising:

an interface; and a processor, wherein:

the interface and/or the processor are configured to provide input data, the processor is configured to determine a result dataset by applying a trained function to the input data including input magnetic resonance data of a local radio-frequency coil, the trained function comprising an artificial neural network (ANN), the input magnetic resonance data is normalized with respect to magnetic resonance data acquired via a radio-frequency body coil by performing a division of magnetic resonance data acquired via the local radio-frequency coil by magnetic resonance data acquired via the radio-frequency body coil for each spatial point, a receive profile of the magnetic resonance data acquired via the radio-frequency body coil is more homogenous than a receive profile of the magnetic resonance data acquired via the local radio-frequency coil, the result dataset includes position information of the local radio-frequency coil, and the interface is further configured to provide the result dataset.

20. A magnetic resonance apparatus, comprising the provision system of claim 19.

* * * * *